(12) United States Patent
Huet et al.

(10) Patent No.: US 9,127,247 B2
(45) Date of Patent: Sep. 8, 2015

(54) PETRI DISH INCLUDING LOCKING MEANS FOR FORMING A STACK

(75) Inventors: Stéphane Huet, Bruz (FR); Jérôme Thepaut, Quebriac (FR); Christophe Gincheleau, Rennes (FR); Frédéric Simon, Combourg (FR); Frank Reverdy, Meillac (FR)

(73) Assignee: AES CHEMUNEX, Combourg (FR)

( * ) Notice: Subject to any disclaimer, the term of this patent is extended or adjusted under 35 U.S.C. 154(b) by 150 days.

(21) Appl. No.: 13/806,091

(22) PCT Filed: May 24, 2011

(86) PCT No.: PCT/EP2011/058452
§ 371 (c)(1),
(2), (4) Date: Dec. 20, 2012

(87) PCT Pub. No.: WO2011/160911
PCT Pub. Date: Dec. 29, 2011

(65) Prior Publication Data
US 2013/0095009 A1    Apr. 18, 2013

(30) Foreign Application Priority Data

Jun. 22, 2010 (FR) .................................... 10 54959

(51) Int. Cl.
*C12M 1/22* (2006.01)
*C12M 3/00* (2006.01)
*B01L 3/00* (2006.01)

(52) U.S. Cl.
CPC ............ *C12M 23/46* (2013.01); *B01L 3/50853* (2013.01); *C12M 23/10* (2013.01); *C12M 23/44* (2013.01); *B01L 3/508* (2013.01); *B01L 2200/025* (2013.01); *B01L 2300/041* (2013.01)

(58) Field of Classification Search
CPC ...... C12M 23/10; C12M 23/22; C12M 23/38; C12M 23/44; C12M 23/46; C12M 23/48; B01L 3/508; B01L 3/50853; B01L 2200/025; B01L 2300/041
USPC ............................ 435/288.3, 305.4; 220/4.27
See application file for complete search history.

(56) References Cited

U.S. PATENT DOCUMENTS 2,077,219 A * 4/1937 Conner .............................. 215/6
3,369,691 A * 2/1968 Tohchung .................... 220/4.27

(Continued)

FOREIGN PATENT DOCUMENTS

DE    10339083 A1    3/2005
EP    0171174 A2    2/1986

(Continued)

*Primary Examiner* — William H Beisner
(74) *Attorney, Agent, or Firm* — Harness, Dickey & Pierce, P.L.C.

(57) ABSTRACT

A Petri dish has members including a receptacle and an additional lid, both having an axisymmetric shape and which are delimited by a bottom wall and at least one peripheral wall, the receptacle and lid bearing complementary lock sections so that when a stack is formed by superposing at least two dishes, borne by a first component of a first dish which can engage with the lock section of the second component of the second dish, thus making them rigidly connected to one another. These lock sections cooperate by relative rotational movement of one dish with respect to the other, the lock sections being borne by the peripheral walls and including protrusions.

14 Claims, 4 Drawing Sheets

(56) References Cited

U.S. PATENT DOCUMENTS

| | | |
|---|---|---|
| 3,704,568 A | 12/1972 | Duhring et al. |
| 3,886,047 A * | 5/1975 | Billups, Jr. ............... 435/305.3 |
| 4,160,700 A | 7/1979 | Boomus et al. |
| 4,170,861 A | 10/1979 | Snyder et al. |
| 4,468,914 A | 9/1984 | Pestes |
| 5,020,297 A | 6/1991 | Borie et al. |
| 6,429,008 B1 | 8/2002 | Copeland et al. |
| 7,105,338 B1 | 9/2006 | Holmes et al. |
| 7,972,842 B2 | 7/2011 | Minton |
| 2011/0243814 A1 | 10/2011 | Brelivet |
| 2012/0061308 A1 | 3/2012 | Gilet et al. |
| 2012/0125483 A1 | 5/2012 | Brelivet |

FOREIGN PATENT DOCUMENTS

| | | |
|---|---|---|
| EP | 1035201 A1 | 9/2000 |
| GB | 886795 A | 1/1962 |
| GB | 2106083 A | 4/1983 |
| GB | 2117788 A | 10/1983 |
| JP | 2003047459 A | 2/2003 |
| JP | 2003102463 A | 4/2003 |
| JP | 2003-225083 A | 8/2003 |

* cited by examiner

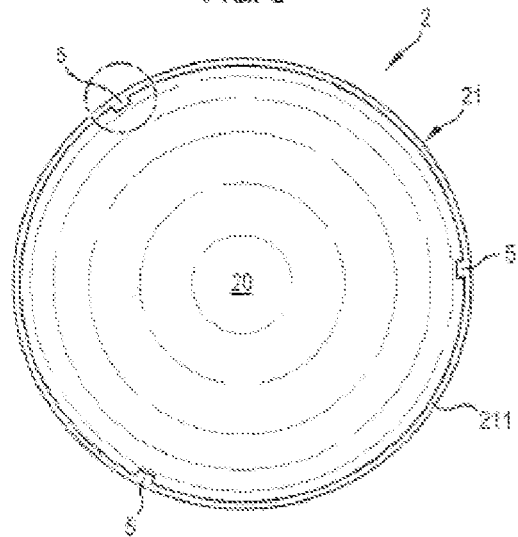
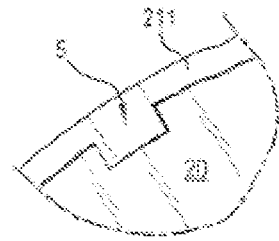
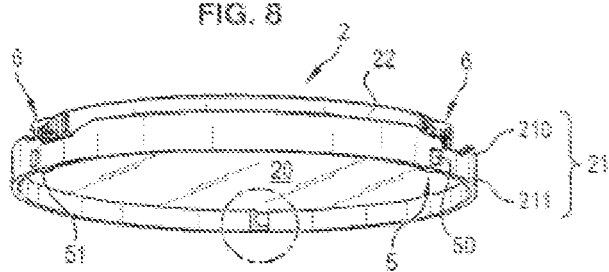
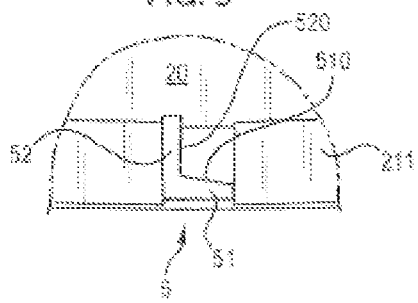

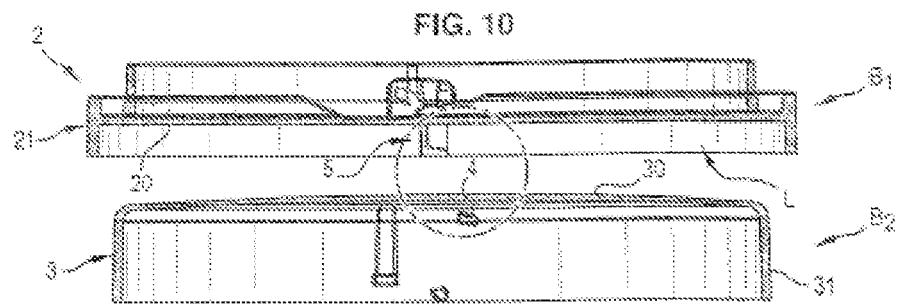
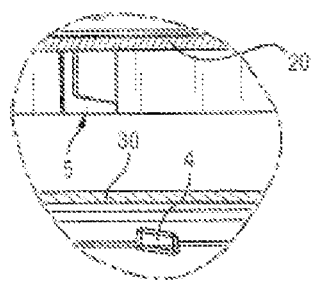
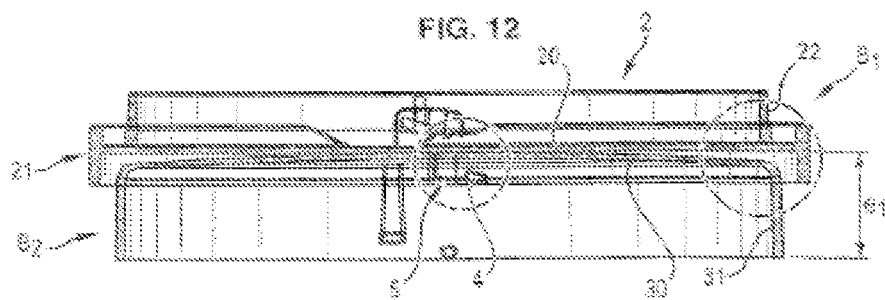
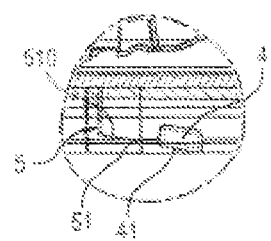 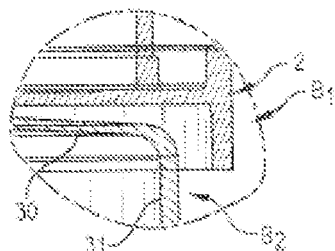

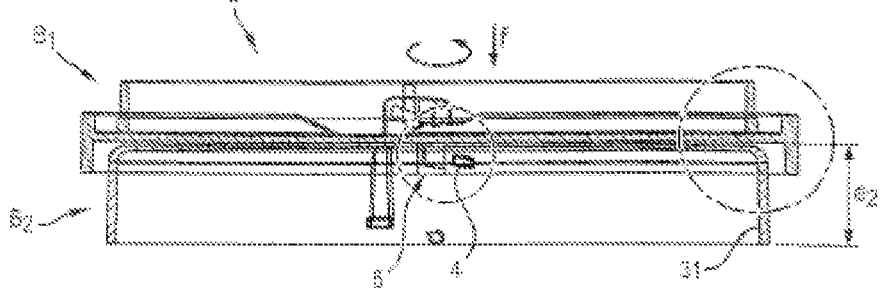
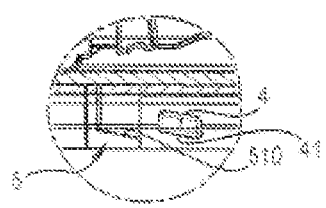
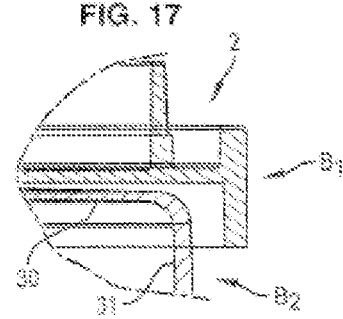
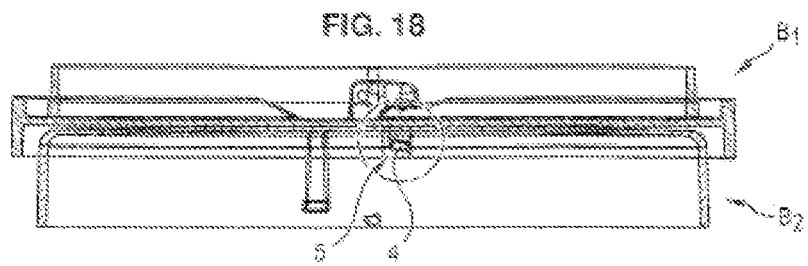
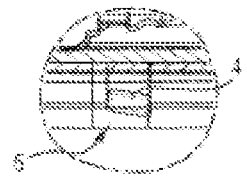

PETRI DISH INCLUDING LOCKING MEANS FOR FORMING A STACK

CROSS-REFERENCE TO RELATED APPLICATIONS

This application is a National Phase Entry of International Application No. PCT/EP2011/058452, filed on May 24, 2011, which claims priority to French Patent Application Serial No. 1054959, filed on Jun. 22, 2010, both of which are incorporated by reference herein.

BACKGROUND AND SUMMARY

The present invention relates to a Petri dish for cultivating micro-organisms, which consists of two members, i.e. a receptacle and an additional lid and which both have a revolution shape.

Such Petri dishes are widely used notably in laboratories and these dishes are provided in order to be superposed so as to form stacks. This notably allows the operators to form different batches of Petri dishes, for example so as to sort them out according to the nature of the culture which is made therein. Documents JP-2003 047459, JP-2003 102463, US-2002/045245 and U.S. Pat. No. 4,160,700 illustrate the state of the art in this matter. However, if this dish stacking function is possible, to this day, there does not exist any means which allows retention of the dishes attached to each other.

Also, up to now, the handling of culture dishes requires the use of transport containers and of external systems for attaching the dishes together. Thus, it is common that the users make use of an elastic or of adhesive tape for securing the dishes together. It is understood that the use of external means involves control of their sanitary quality, and therefore of their sterilization. In certain cases, these constraints for handling and transporting Petri dishes are solved by using an additional disposable transport tool, thereby allowing the displacement of a batch of dishes from one place to another, which in all the scenarios involves an additional cost.

The present invention has the object of solving these difficulties. For this purpose, it proposes a Petri dish which consists of two members, i.e. a receptacle and an additional lid, which both have an axisymmetrical shape (revolution shape) and which are each delimited by a bottom wall and at least one peripheral wall, that said receptacle and lid bearing additional locking means laid out so that, upon forming a stack formed with the superposition of at least two dishes, the locking means borne by a first member of a first dish may cooperate with locking means of the second member of the second dish, making them thus interdependent on each other, one of said members including a peripheral wall which extends above and below the bottom wall, while the other one is dimensioned so that, upon forming said stack, said member of a first dish is partly engaged into the other member of a second dish, in a housing delimited by the bottom wall and a portion of said wall, characterized by the fact that said additional locking means are able to cooperate by a relative rotary movement of one dish relatively to the other, that said locking means are borne by the peripheral walls and that they consist in protrusions. Thus, according to the invention, the members which make up each of the Petri dishes integrate within themselves means for locking to another dish. By their presence, it is therefore possible to form stacks of dishes, in which each dish is made interdependent on its neighbor(s) so as to form an assembly which may be handled without any other external connection means.

According to advantageous and non-limiting characteristics of this dish:
said protrusions are at least two in number, are angularly equidistant and extend over an angular fraction of said wall;
said protrusions have the shape of portions of mating (complementary) helicoidal ribs;
the bottom wall of one of said members bulges outwards and is elastically deformable so that it occupies a substantially planar position. Other characteristics and advantages of the present invention will become apparent upon reading the detailed description which follows, of a preferential embodiment.

BRIEF DESCRIPTION OF THE DRAWINGS

This description will be made with reference to the appended drawings wherein:
FIG. 2 is a side view of the lid of such a Petri dish, while
FIG. 4 is a top view of the lid of FIG. 4, while
FIG. 6 is a bottom view of a receptacle of a Petri dish according to the invention, while
FIG. 7 is an enlarged view of the area marked by a circle in the previous figure;
FIG. 8 is a perspective view of the receptacle of FIG. 6 while
FIG. 9 is an enlarged view of the area marked by a circle in the previous figure;
FIGS. 10, 12, 15 and 18 are cross-sectional views of the receptacle of a dish $B_1$ and of the lid of a dish $B_2$, in different positions which finally lead to their being interdependent on each other;
and
FIGS. 11, 13, 14, 16, 17 and 19 are detailed views of the areas marked by a circle in the figures located just above.

DETAILED DESCRIPTION

Figure 1:
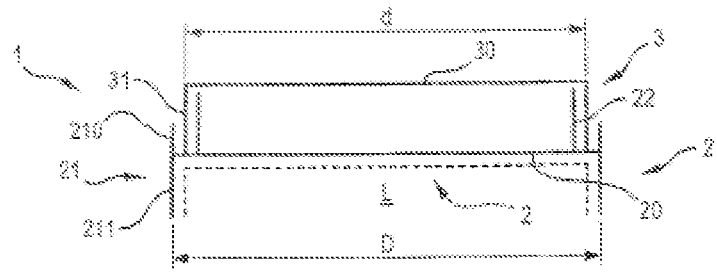
FIG. 1 is a very schematic view, according to a diametrical sectional view, of a Petri dish structure according to the invention.

The present invention most particularly applies to a Petri dish such as the one which is very schematically illustrated in FIG. 1. Like all Petri dishes, the latter consists of two members, i.e. a receptacle 2 and an additional lid 3 and both have a revolution shape. They are for example made in transparent plastic material such as crystalline polystyrene.

The receptacle 2 includes a generally planar bottom wall 20 which is surrounded by a peripheral wall 21. As shown in this figure, this wall extends both above and below the plane in which the bottom wall 20 is contained, in order to form an upper wall portion 210 and a lower wall portion 211. In the embodiment shown, the bottom wall 20 also includes another wall 22, a so called "inner wall", so that there exists an annular space between both aforementioned coaxial walls. The bottom wall 20 delimits with the inner wall 22 the space in which a culture medium is deposited.

The lid 3 consists of a bottom wall 30 and of a peripheral wall 31. The latter is dimensioned so as to be able to be positioned against the bottom wall 20 of the receptacle 2, between the walls 21 and 22. These receptacle 2 and lid 3 may include means not shown which allow them to be immobilized relatively to each other.

Under the letter L is referenced in this figure, an open housing which is delimited by the bottom wall 20 of the receptacle and the lower portion 211 of the wall 20. This housing has a diameter D. The lid 3 is as for it dimensioned so as to have a diameter d such that this lid may be inserted into the annular space located between the walls 21 and 22, as already mentioned, but in such a way that the lid of another identical dish may be inserted into the aforementioned housing L.

This is the situation shown in FIG. 1 wherein the lid of the second dish is illustrated as a profile in dashed lines. This dish configuration is a traditional configuration. However, in certain embodiments not shown the structure of the receptacle 2 and of the lid 3 may be inverted. In other words, by flipping FIG. 1 by 180°, the lid referenced as 3 would be formed by the receptacle 2 and vice versa.

Figure 2:
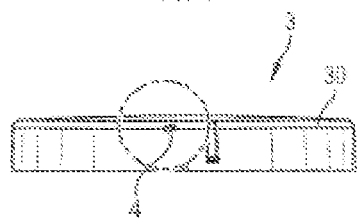
Figure 4:
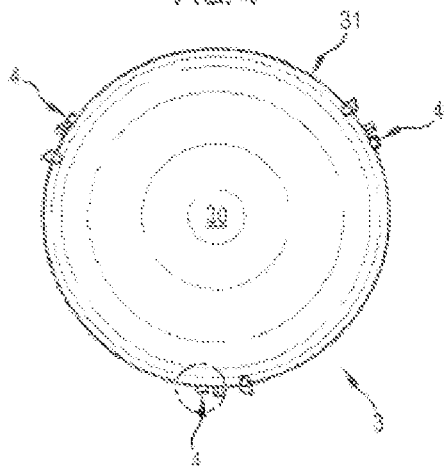
Figure 5:
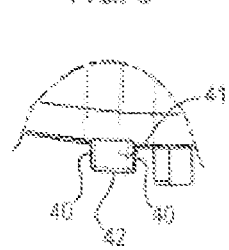
FIG. 5 is an enlarged view of the area marked with a circle in the previous figure.

In the embodiment of FIGS. 2 and the following figures, the lid 3 has on its peripheral wall 31, protrusions or nipples referenced as 4. One is dealing here with a lid which includes three identical and angularly equidistant protrusions 4, as this is well visible in FIG. 4. These protrusions extend radially outwards while originating on the external face of the wall 31. They have two upper and lower faces 41 parallel and tilted by an acute angle a relatively to the horizontal. Both of their vertical lateral faces are referenced as 40, and their end face as 42.

Now referring to FIGS. 6 to 9, it is seen that the receptacle 2 also includes the same number of additional radial protrusions 5, which are borne by the lower portion 211 of the wall 2 and turned towards the inside of the dish. Seen from the front, these protrusions assume an L-shape, with a base 51, the upper face 510 of which is extending upwards, and with a vertical branch 52, the face 520 of which forms an abutment. The transverse extension of these protrusions is provided so that, if a receptacle 2 and a lid 3 are superposed, the additional protrusions 4 and 5 interfere when they are brought closer to each other. In some way, the protrusions 4 and 5 which have just been shown, have the shape of a portion of complementary helicoidal ribs.

In FIGS. 10 and 12, the receptacle 2 of a first Petri dish $B_1$ as well as the lid 3 of a second Petri dish $B_2$ are illustrated. These figures show the relative positions of both of these members, when it is desired to make them interdependent on each other. Of course, in practice, the receptacle 2 of the dish $B_1$ is covered with its lid 3, while the lid 3 of the dish $B_2$ is assembled to its receptacle 2. The latter however has not been illustrated in the figures in order not to unnecessarily burden them.

Figure 3:
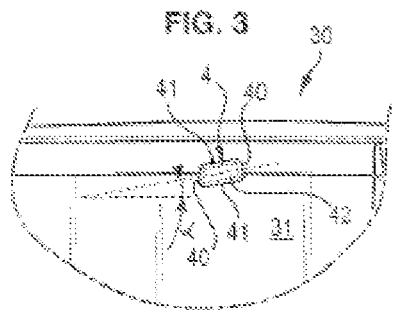
FIG. 3 is an enlarged view of the area marked by a circle in the previous figure.

It will be noted, with reference to FIG. 10, that the bottom wall 30 of the lid 3 slightly bulges, with a convexity turned towards the outside of said lid, this bottom wall having the capability of being elastically deformable when pressure is exerted on said wall. In other words, subject to such pressure, it has the capability of being brought back into a position where it is substantially planar. It should be noted that in FIG. 10 and the following figures, the protrusions 4 which equip the lid 3 are seen in transparency, which explains that they have an inverted orientation with respect to that of FIGS. 2 and 3, in which they are seen from the outside of said lid.

With reference to FIGS. 10 and 11 and with view to forming a stack of dishes, two dishes $B_1$ and $B_2$ are brought closer together so that the lid 3 of the lower dish $B_2$ partly enters the housing L of the receptacle 2 of the upper dish $B_1$ and the protrusions 4 and 5 do not coincide vertically (in other words they are not found vertically below each other). This is illustrated in FIG. 10. This closing-in movement continues until the bottom wall 30 of the lid 3 abuts against the bottom wall 20 of the receptacle 2. In this position, the lid 2 has a rated height $e_1$ and which corresponds to the cumulated height of the wall 31 and of the bottom wall 30, because of its slightly curved shape.

Referring to FIGS. 13 and 14, it is then seen that the face 510 of the protrusion 5 is at a slightly upper level than that of the lower face 41 of the protrusion 4 so that even if a rotary movement is imparted to one of the dishes, relatively to each other, said protrusions cannot cooperate but on the contrary will abut against each other. On the other hand, and as illustrated in FIG. 15 by applying pressure on the upper dish $B_1$, the deformation of the bottom wall 30 of the lid 3 is made so that the latter from now on occupies a rated height $e_2$ of less than the height $e_1$. By doing this, said faces 510 and 41 are at the same level, so that by a rotary movement of a dish relatively to the other, it is possible to engage the protrusion 4 into the protrusion 5.

The tilted orientation of the faces 41 and 510, in the fashion of portions of helicoidal ribs, facilitates this engagement. Of course, one skilled in the art will be able to adapt the dimensions and the relatively positions of the protrusions 4 and 5 so that they cooperate intimately.

Finally, the situation of FIG. 18 is then attained in which both protrusions are engaged into each other. It will be noted that the vertical branch of the protrusion 5 forms an abutment which prevents any continuation of the rotary movement of one dish relatively to the other, so that the protrusions are locked in this condition. By exerting traction on one dish relatively to the other, in a direction generally perpendicular to their bottom wall, it is absolutely impossible to detach them from each other. Such a detachment can only be applied voluntarily, by performing a rotary movement in the opposite direction to the one which was performed earlier. By making use of the means described above, it is therefore possible to form stacks of Petri dishes which are made interdependent on each other, two by two, so that it is possible to envision the lifting of such a stack simply by grasping the upper dish of the stack.

Of course, the present invention applies to all the structures of Petri dishes which include additional locking means borne by the members formed by the receptacle and the lid. In the example described above, the lower portion 211 of the wall 21 of the receptacle 2 is intended to be continuous. However, nothing prevents certain areas from having discontinuities notably in order to lighten said Petri dish at the most.

The invention claimed is:

1. A Petri dish comprising members including a receptacle and a lid, both of which have a cylindrical shape and which are delimited by a bottom wall and at least one peripheral wall, each of said receptacle and said lid including a lock section laid out so that, upon forming a stack formed with superposition of at least two of said Petri dishes, said lock section borne by a first of said members of a first of said Petri dishes cooperate with said lock section of a second of said members of a second of said Petri dishes, making said first member of said first Petri dish and said second member of said second Petri dish thus interdependent on each other, said peripheral wall of said second member extending above and below said bottom wall while said first member is dimensioned so that, upon forming said stack, said first member of said first Petri dish is partly engaged into said second member of said second Petri dish, in a housing delimited by said bottom wall and a portion of said peripheral wall, said lock sections cooperating by a rotational movement of one of said Petri dishes relative to the other one, and said lock sections being borne by said peripheral walls of said receptacle and said lid and including protrusions.

2. The dish according to claim 1, wherein said protrusions are at least two in number, are angularly equidistant and extend over an angular fraction of said peripheral walls.

3. The dish according to claim 1, wherein that said protrusions have shapes of portions of mating helicoidal ribs.

4. The dish according to claim 1, wherein said bottom wall of one of said members bulges outwards and is elastically deformable so that it occupies a substantially planar position.

5. The dish according to claim 4, wherein when pressure is applied to one of said Petri dishes, said bottom wall of the one of said members elastically deforms to position said lock sections relative to one another such that one of said Petri dishes is rotatable relative to the other one of said Petri dishes to engage said lock sections with one another.

6. The dish according to claim 1, wherein said protrusions include a first protrusion extending radially outward from said peripheral wall of said lid, and a second protrusion extending radially inward from said peripheral wall of said receptacle.

7. The dish according to claim 1, wherein at least one of said protrusions includes a vertical branch that acts as a stop when the other one of said protrusions abuts said vertical branch, thereby preventing further rotational movement of one of said Petri dishes relative to the other one.

8. A Petri dish comprising:
   a receptacle including a bottom wall, a peripheral wall, and a protrusion extending from the at least peripheral wall; and
   a lid configured to cover at least a portion of the receptacle to define an enclosed space, the lid including a bottom wall, a peripheral wall, and a protrusion extending from the peripheral wall of the lid, wherein when a first of said Petri dish is stacked on top of a second of said Petri dish such that said receptacle of said first Petri dish is on top of said lid of said second Petri dish, one of said receptacle of said first Petri dish and said lid of said second Petri dish is rotatable relative to the other one of said receptacle of said first Petri dish and said lid of said second Petri dish to engage said protrusions with one another and thereby prevent detaching said Petri dishes from one another by exerting a force on one of said Petri dishes relative to the other one of said Petri dishes in a direction perpendicular to said bottom walls of said Petri dishes.

9. The dish according to claim 8, wherein said protrusion on said lid extends radially outward from said peripheral wall of said lid, and said protrusion on said receptacle extends radially inward from said peripheral wall of said receptacle.

10. The dish according to claim 8, wherein at least one of said protrusions includes a vertical branch that acts as a stop when the other one of said protrusions abuts said vertical branch, thereby preventing further rotational movement of the one of said receptacle of said first Petri dish and said lid of said second Petri dish relative to the other one of said receptacle of said first Petri dish and said lid of said second Petri dish.

11. The dish according to claim 8, wherein said peripheral wall of said receptacle extends above and below said bottom wall of said receptacle, and said receptacle further includes an inner wall that cooperates with the peripheral wall of said receptacle to define an annular space located therebetween.

12. The dish according to claim 11, wherein said lid is dimensioned so that said peripheral wall of said lid is insertable into the annular space located between said peripheral wall of said receptacle and said inner wall of said receptacle.

13. The dish according to claim 8, wherein said bottom wall of said lid bulges outwards and is elastically deformable so that it occupies a substantially planar position.

14. The dish according to claim 13, wherein when downward pressure is applied to said first Petri dish, said bottom wall of said lid of said second Petri dish elastically deforms to position at least part of said protrusion on said receptacle of said first Petri dish below said protrusion on said lid of said second Petri dish such that one of said receptacle of said first Petri dish and said lid of said second Petri dish is rotatable relative to the other one of said receptacle of said first Petri dish and said lid of said second Petri dish to engage said protrusions with one another.

* * * * *